(12) United States Patent
Szczepaniak et al.

(10) Patent No.: US 10,149,629 B2
(45) Date of Patent: Dec. 11, 2018

(54) MEASURING SYSTEM FOR A PROBE

(71) Applicant: PIT-RADWAR Spółka Akcyjna, Warsaw (PL)

(72) Inventors: Zenon Szczepaniak, Warsaw (PL); Mariusz Łuszczyk, Minsk (PL)

(73) Assignee: PIT-RADWAR SPOLKA AKCYJNA, Warsaw (PL)

( * ) Notice: Subject to any disclaimer, the term of this patent is extended or adjusted under 35 U.S.C. 154(b) by 733 days.

(21) Appl. No.: 14/781,372

(22) PCT Filed: Apr. 19, 2013

(86) PCT No.: PCT/PL2013/000055
§ 371 (c)(1),
(2) Date: Sep. 30, 2015

(87) PCT Pub. No.: WO2014/098629
PCT Pub. Date: Jun. 26, 2014

(65) Prior Publication Data
US 2016/0073923 A1 Mar. 17, 2016

(30) Foreign Application Priority Data
Dec. 21, 2012 (PL) .......................................... 402181

(51) Int. Cl.
*A61B 5/00* (2006.01)
*A61B 5/05* (2006.01)
(Continued)

(52) U.S. Cl.
CPC ............ *A61B 5/0507* (2013.01); *A61B 5/053* (2013.01); *A61B 5/14532* (2013.01); *A61B 2503/40* (2013.01); *A61B 2562/0228* (2013.01)

(58) Field of Classification Search
CPC .... A61B 5/0507; A61B 5/053; A61B 5/14532
See application file for complete search history.

(56) References Cited

U.S. PATENT DOCUMENTS

| 4,829,233 A | * | 5/1989 | Flemming | ............. | G01N 22/00 |
| | | | | | 324/632 |
| 5,335,668 A | * | 8/1994 | Nardella | ............. | A61B 5/0535 |
| | | | | | 600/547 |

(Continued)

FOREIGN PATENT DOCUMENTS

| GB | 2455722 | 6/2009 |
| WO | 2006138382 A2 | 12/2006 |

OTHER PUBLICATIONS

International Search Report and Written Opinion, PCT/PL2013/000055, dated Jul. 5, 2013.

*Primary Examiner* — Tse Chen
*Assistant Examiner* — Joanne Hoffman
(74) *Attorney, Agent, or Firm* — Wenderoth Lind & Ponack, L.L.P.

(57) ABSTRACT

A measuring system for probe, especially one for measuring dielectric properties and used in devices for measuring properties of dielectric constant changes in human or animal tissues, characterized in that it comprises a microwave resonance circuit (3) made on dielectric substrate and shaped in the form of a three-stage resonator composed of three segments of striplines with different impedances of each of the segments and arranged with respect to each other is such a way that successive segments are perpendicular to each other, and further comprises rows of grommets (2) with metallized surfaces connecting front surfaces on both sides of the substrate and constituting the earth of the probe.

4 Claims, 3 Drawing Sheets

(51) Int. Cl.
*A61B 5/053* (2006.01)
*A61B 5/145* (2006.01)

(56) References Cited

U.S. PATENT DOCUMENTS

| | | |
|---|---|---|
| 6,219,565 B1 | 4/2001 | Cupp et al. |
| 6,565,558 B1 | 5/2003 | Lindenmeier et al. |
| 6,954,662 B2 | 10/2005 | Freger et al. |
| 8,032,211 B2 | 10/2011 | Hashimshony et al. |
| 8,133,178 B2 | 3/2012 | Brauker et al. |
| 8,229,535 B2 | 7/2012 | Mensinger et al. |
| 8,882,670 B2 | 11/2014 | Hancock |
| 2004/0065158 A1* | 4/2004 | Schrepfer ............... A61B 5/05 73/864.81 |
| 2008/0319285 A1* | 12/2008 | Hancock ............... A61B 5/05 600/309 |
| 2010/0298680 A1 | 11/2010 | Talary et al. |
| 2012/0095307 A1* | 4/2012 | Caduff ............... A61B 5/0531 600/347 |

\* cited by examiner

MEASURING SYSTEM FOR A PROBE

The subject of this invention is a measuring system for probe, especially one measuring dielectric properties, to be used in devices for measurement of dielectric constant changes in human or animal tissues. A probe with such system allows to perform non-invasive contact measurement of blood sugar in humans through measurement of changes in dielectric constant of tissues.

Description of invention application US 2004/0065158 A1 reveals a solution in which to measure the glucose level in blood or tissues, a probe in the form of two electrodes is used that constitutes a capacitor in resonance circuit of the measuring system. Changes of glucose level in blood result in changes of electric capacity and thus also change the resonance frequency of the resonance circuit. One of the electrodes (electrode A) has the form of a ring fixed to the probe casing. The second electrode (electrode B) has the form of a metallized strip with length much greater then width made on dielectric base and located inside the probe. The probe is constructed in such a way that electrode A adheres closely to the examined tissue, while electrode B remains isolated from both the tissue and electrode A.

A flaw of the solution according to the above-quoted invention is the necessity to maintain significant dimensions of inner electrode B in order to ensure sufficient the level of coupling with the examined tissue. The level of coupling has a direct effect on precision of measurement. Electrode dimensions translate to overall dimensions of the measuring probe.

The aim of the present invention is to provide a measuring system for a probe with small overall dimensions that would maintain high sensibility and accuracy of measurements of dielectric properties changes occurring in examined tissues.

This aim was achieved in solution according to the present invention in which the probe measuring system comprises a microwave resonance circuit placed on a dielectric substrate and given the form of a three-stage resonator composed of three segments of striplines with impedances different for each of the segments. The segments are positioned in such a way that the first segment is perpendicular to the second segment, which in turn is perpendicular to the third segment. The measuring system comprises also rows of grommets with metallized surfaces that are located on both sides of the dielectric substrate and constitute the probe's earth. Further, the measuring system includes also the microwave signal input located of the surface opposite to the surface containing the resonance circuit.

Striplines of individual elements of the probe measuring system have different values of complex impedance selected in such a way that the resonance frequency in the range from 2.5 GHz to 3.5 GHz is obtained.

The measuring system has the dielectric substrate made of polytetrafluoroethylene (PTFE) laminate.

The measuring system has the upper surface of its dielectric substrate metallized primarily with copper and secondarily with gold.

Individual segments of the measuring system are arranged in the form of letter U.

The measuring system has an output from the microwave resonance circuit connected with the probe's coaxial connector of SMB type.

In the measuring system, the microwave resonance circuit is located centrally, and rows of grommets are arranged annularly around it, whereas the dielectric substrate has the form of a circle.

The measuring system according to the invention is preferably characterized with that the substrate on which the resonance circuit was made is made of a dielectric material, i.e. it does not absorb water and is hydrophobic, which eliminates the measurement error related to excessive amount of moisture between the probe and examined tissue. Moreover, the dielectric substrate is also hypoallergic, i.e. it does not induce skin irritation in the place of contact. Gold coating is an additional protection against irritation.

The subject of the present invention is shown in an example embodiment in figures, of which FIG. 1 shows the measuring system in a view from the side of the contact with tissue;

Figure 1:
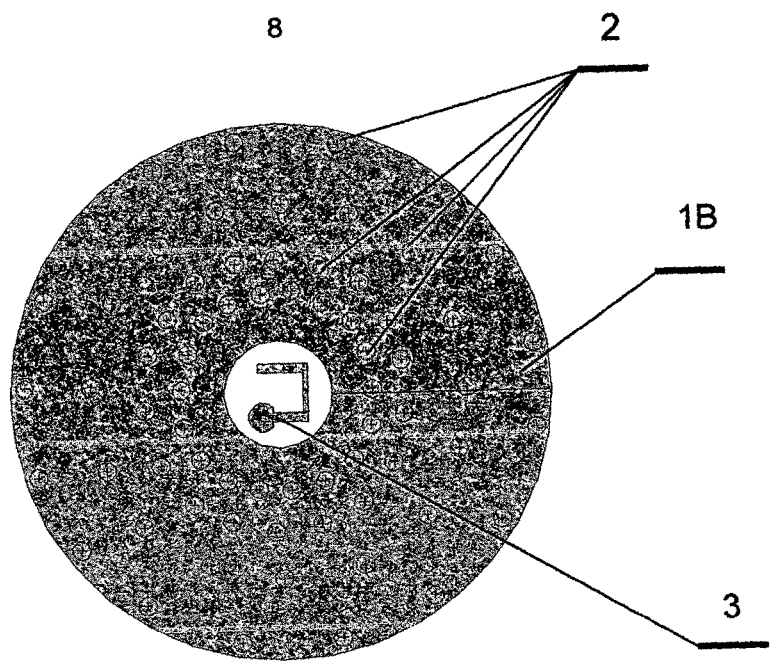
Figure 2:
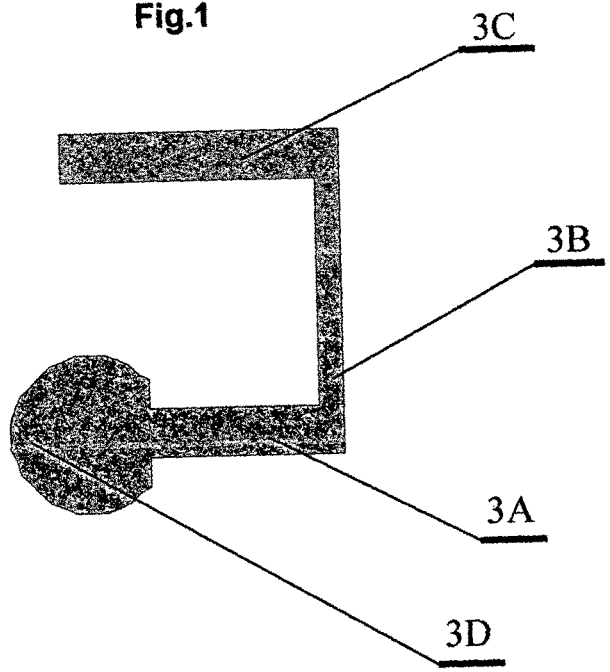
FIG. 2 shows the arrangement of resonator striplines.
Figure 3:
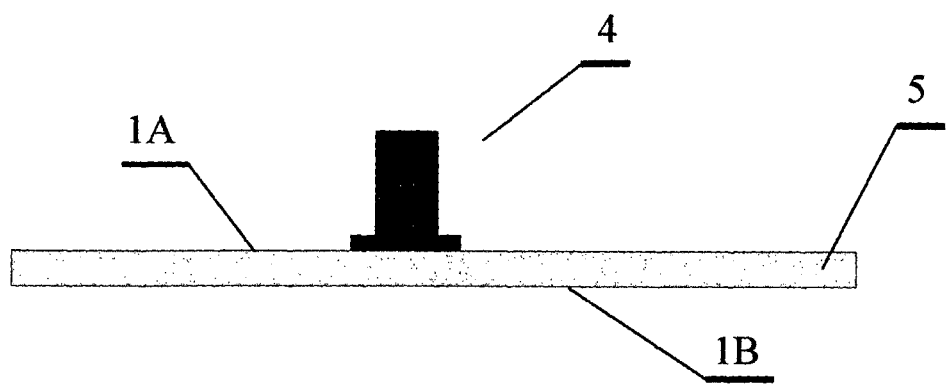
FIG. 3 shows the resonance circuit with coaxial connector of SMB type in the side view.

The measuring system was made on a circle of PTFE laminate constructed as the dielectric layer 5 with the following parameters: dielectric constant $\varepsilon_r$=2.5, substrate thickness h=0.635 mm, dielectric loss angle tangent tg($\delta$)=0.0001, and metallization layer 1 with copper thickness t=18 μm. The measuring probe diameter is 30 mm. Surface 1A of dielectric layer 5 is completely coppered with layer of gold sputtered on it. From this side, the system is supplied with microwave signal by means of coaxial connector 4 of SMB type. The coaxial connector is mounted on the circle in such a way that its sting is insulated from the copper coat and connected with the microwave resonance circuit 3 located in the other side of the circle. Resonance circuit in the form of three-stage resonator is located centrally on the surface of contact with tissue and is made in the form of three segments of stripline.

Each of the segments is characterized with different values of their complex impedances, modules and phases of which for segments 3A, 3B, and 3C are: $Z_{0A}$=32.5Ω and $\varphi_A$=53°; $Z_{0B}$=35Ω and $\varphi_B$=58°; and $Z_{0C}$=31.5Ω and $\varphi_C$=60°, respectively, for the resonance frequency of 3.3 GHz.

The earth of the system in the form of upper surface 1A and lower surface 1B of dielectric substrate 5 that are connected by means of metallized grommets 2. The number and location of grommets is of no importance from the point of view of the invention essence, whereas it is important that appropriately large number of grommets ensures connection of earthed surfaces on both sides of the measuring system.

Figure 4:
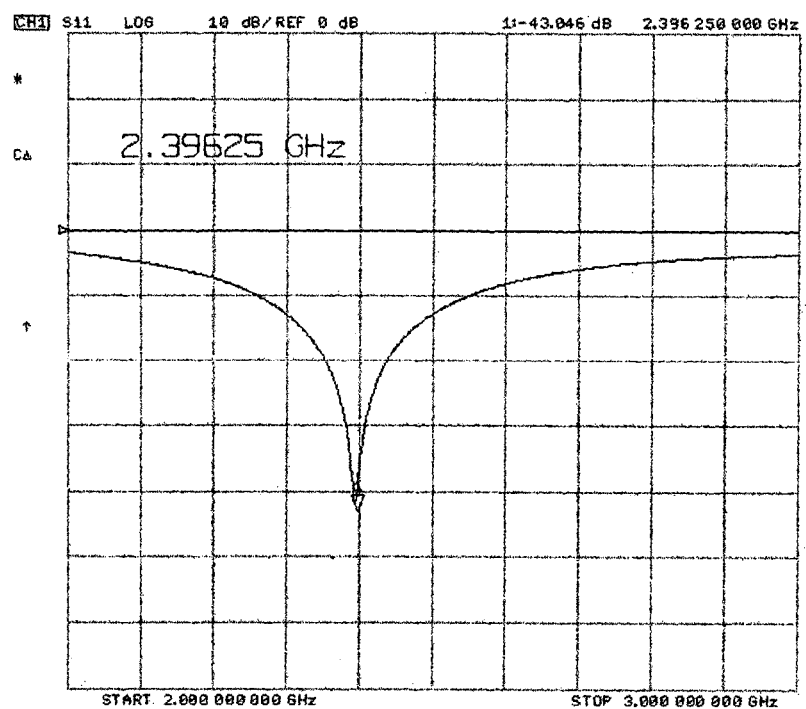
FIG. 4 shows, in the form of a graph, an example measured reflection coefficient characteristics of the microwave probe in contact with skin of a human forearm.
Figure 5:
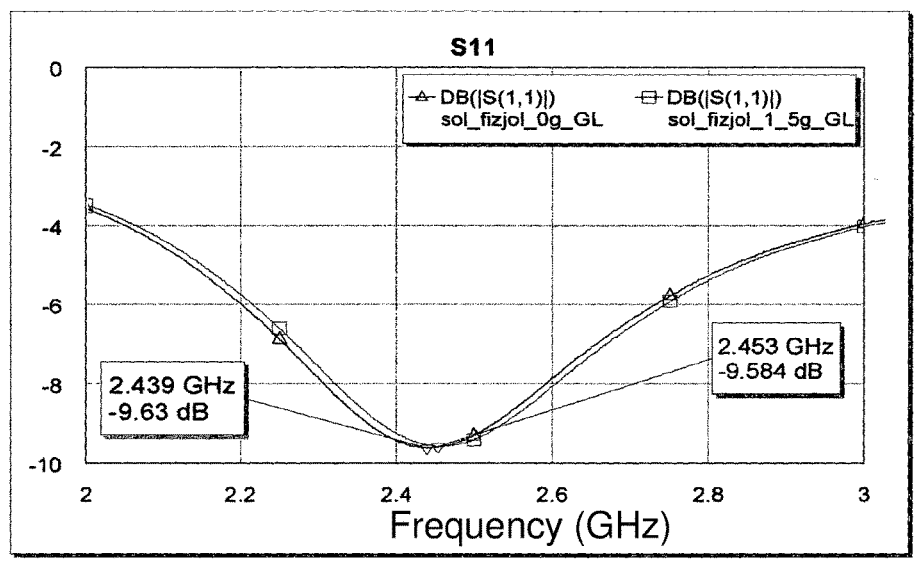
FIG. 5 shows measured reflection coefficient characteristics of the microwave probe for different solutions of physiological salt with glucose (0 and 500 mg/dl) and described in the following.

From the point of view of description of its electric properties, the probe with the measuring system is a one-port element. Such circuit is characterized with the reflection coefficient represented by S11 in matrix representation. The reflection coefficient value for the probe with the measuring system as described in the example embodiment remaining in contact with skin on forearm of a human is presented by the graph in FIG. 4 where the minimum reflection coefficient value of the circuit occurs for the frequency 2.3 GHz. On the other hand, differences depending on composition of the examined solution are plotted in FIG. 5. The characteristics representing variation of modulus of the reflection coefficient—parameter |S11| as a function of microwave signal frequency change shows the resonance curve of the measuring probe resonance circuit.

The probe measuring system is designed to be applied in non-invasive examination of blood sugar changes in humans and properties of dielectric constant changes in human or animal tissues.

The invention claimed is:

1. A measuring system for a probe for measuring dielectric properties and used in a device for measuring properties of dielectric constant changes in human or animal tissues, the measuring system comprising:
   a microwave resonance circuit placed on a dielectric substrate, the microwave resonance circuit being shaped in the form of a three-stage resonator composed of three segments of striplines, the three segments including a first segment, a second segment, and a third segment,
   wherein the first segment, the second segment, and the third segment have different values of a complex impedance, the different values of the complex impedance being selected so that a resonance frequency in the range from 2.5 GHz to 3.5 GHz is obtained,
   wherein the three segments are arranged with respect to each other in such a way that (i) the first segment is connected with an output of the microwave resonance circuit, (ii) the first segment is connected to and perpendicular to the second segment, and (iii) the second segment is connected to and perpendicular to the third segment,
   wherein the measuring system further comprises rows of grommets with metallized surfaces connecting a first surface located on a first side of the dielectric substrate with a second surface on a second side of the dielectric substrate, the first surface and the second surface being on opposite sides of the dielectric substrate and constituting the probe's earth,
   wherein the dielectric substrate has the form of a circle, the microwave resonance circuit being located on the first surface of the dielectric substrate, and the grommets are arranged annularly around the microwave resonance circuit,
   wherein the measuring system is supplied with a microwave signal by means of a coaxial connector of an SMB type, and
   wherein the coaxial connector is mounted on the second side of the dielectric substrate in such a way that a sting of the coaxial connector is insulated from a copper coat and connected with the microwave resonance circuit located on the first side of the dielectric substrate.

2. The measuring system for probe according to claim 1, wherein the dielectric substrate is a polytetrafluoroethylene laminate.

3. The measuring system for probe according to claim 1, wherein the second surface, which is opposite to the first surface on which the microwave resonance circuit is located, is metallized, primarily with copper and secondarily with gold.

4. The measuring system for probe according to claim 1, wherein the three segments are arranged in a U shape with respect to the output of the microwave resonance circuit.

* * * * *